(12) United States Patent
Tang et al.

(10) Patent No.: US 8,131,042 B2
(45) Date of Patent: Mar. 6, 2012

(54) METHODS AND APPARATUS FOR HYBRID CONE BEAM IMAGE RECONSTRUCTION

(75) Inventors: Xiangyang Tang, Waukesha, WI (US); Jiang Hsieh, Brookfield, WI (US); Fang Dong, New Berlin, WI (US); Jiahua Fan, Waukesha, WI (US); Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1063 days.

(21) Appl. No.: 12/028,543

(22) Filed: Feb. 8, 2008

(65) Prior Publication Data

US 2009/0202126 A1   Aug. 13, 2009

(51) Int. Cl.
*G06K 9/00* (2006.01)
(52) U.S. Cl. ........................................ 382/131; 378/901
(58) Field of Classification Search .................. 382/128, 382/131; 378/4, 15, 901
See application file for complete search history.

(56) References Cited

U.S. PATENT DOCUMENTS

| 5,663,995 | A | * | 9/1997 | Hu .................................. 378/15 |
| 6,014,419 | A | | 1/2000 | Hu |
| 6,272,200 | B1 | | 8/2001 | Pan et al. |
| 6,504,892 | B1 | | 1/2003 | Ning |
| 6,507,633 | B1 | | 1/2003 | Elbakri et al. |
| 6,625,249 | B1 | | 9/2003 | Temkin et al. |
| 6,850,587 | B1 | | 2/2005 | Karimi et al. |
| 7,006,591 | B2 | | 2/2006 | Machida |
| 7,245,755 | B1 | | 7/2007 | Pan et al. |
| 7,272,429 | B2 | | 9/2007 | Walker et al. |

* cited by examiner

*Primary Examiner* — Jurie Yun
(74) *Attorney, Agent, or Firm* — The Small Patent Law Group; Dean D. Small

(57) ABSTRACT

A method for reconstructing an image using an imaging apparatus that includes a radiation source, a detector array, and a computer. The method includes performing a helical scan of an object at a selected helical pitch using the radiation source and detector array to obtain image data, and reconstructing an image of the object utilizing the computer programmed to perform a hybrid cone beam image reconstruction having ray-wise 3D weighting, wherein the weighting is dependent upon both helical pitch and z-distance.

20 Claims, 10 Drawing Sheets

METHODS AND APPARATUS FOR HYBRID CONE BEAM IMAGE RECONSTRUCTION

BACKGROUND OF THE INVENTION

This invention relates generally to hybrid cone beam image reconstruction, especially image reconstruction in volumetric computed tomography (VCT).

Diagnostic computed tomographic (CT) images are acquired in both axial and helical scans in clinical applications. In both single detector-row CT (SDCT) and multiple detector-row CT (MDCT), a helical scan can provide better longitudinal spatial resolution, faster patient throughput and better patient comfort relative to an axial scan because the patient table proceeds continuously and smoothly during the scan. In cone beam VCT, in addition to the benefits mentioned above, the helical scan can provide better image quality than an axial scan because it satisfies the so-called data sufficiency condition. Therefore, helical scans have played a dominant role in most clinical applications using SDCT, MDCT and VCT.

In a helical scan of SDCT, if projection data corresponding to a 360° view angle range are utilized to reconstruct one image, the z-location of an image plane is usually determined by an interception of the image plane and the helical source trajectory, which is located at the mid-way of the 360° view angle range. Thus, if a scan, as represented by the motion 102 of a radiation source 14 around a slice 104 of an object 22 in prior art FIG. 1, spans only one helical turn corresponding to 360° in view angle range (i.e., a single helical turn), only one image is reconstructed. Referring to prior art FIG. 2, if more than one image (of, e.g., a plurality of slices 104) is to be reconstructed, the helical scan 102 has to span more than one turn (i.e., multiple helical turns), in which each image plane or slice corresponds to a 360° view angle range. Consequently, the total projection view angle range is determined by the union of a family of 360° view angle ranges corresponding to each image plane. The 360° view angle ranges for each image plane overlap one another substantially, and the first image 106 and the last image 108 are prescribed at the locations that are indented by one half helical turn from the starting point 110 and ending point 112 of the scan, respectively. The indention in image location on each end of the scan corresponds to a 180° view angle range. Due to the indentions, the imaging zone (106-108) is smaller than the scan zone (110-112), and the total difference between these zones corresponds to a view angle range of 360°. The difference between the scan zone and the image zone is hereafter referred to as the over-beaming zone. If the helical source trajectory is mathematically expressed as $$ST(\beta) = \left(R\sin\beta,\ R\cos\beta,\ \frac{H}{2\pi}\beta\right),\quad \beta \subseteq [\beta_s, \beta_e], \tag{1}$$

where $\beta$ is an angle of rotation of radiation source 14, $\beta_s$ is the starting angle of the scan, $\beta_e$ is the ending angle of the scan, R is the radial distance of radiation source 14 from a central axis of the scan, and H is the distance proceeded by the patient table during one helical turn. The scan zone is $[\beta_s, \beta_e]$. The image zone can be defined as $[\beta_s+\pi, \beta_e-\pi]$. Note that the total dimension of the over-beaming zone along the z-direction is equal to H.

Prior art helical scans in both MDCT and VCT have so far used similar strategies for determining scan zone and image zone in diagnostic CT imaging. However, modern MDCT and VCT are being produced with increasing numbers of detector rows. As the number of detector rows increases, the over-beaming zone increases linearly and must be addressed appropriately. For example, in an SDCT embodiment having a detector row width of 0.625 mm, a typical helical scan may be carried out at pitch 1:1. The over-beaming zone is equal to the distance proceeded by the patient table during one helical turn, i.e., 0.625 mm in this example. A typical helical scan may be carried out at pitch 16/16:1 using a 16 detector-row MDCT with an identical detector row width, 0.625 mm. The over-beaming zone in this MDCT example is 16×0.625=10.0 mm. Thus, anatomic structures within a 10.0 mm zone may be irradiated by x-ray source 14 in a 16 detector-row MDCT, but no images corresponding to the structures in this zone are reconstructed. With even larger number of detector rows utilized in cone beam VCT, e.g., 64 detector row at width 0.625 mm, the over-beaming zone may increase to 64×0.625=40.0 mm if the helical scan is conducted at pitch 64/64:1.

Diagnostic volumetric CT will ultimately be provided by imaging system embodiments having even larger numbers of detector rows. Therefore, if no appropriate measures are exercised, the x-ray dose rendered to the over-beaming zone becomes significant from the perspective of ALARA (as low as reasonably achievable) principle.

BRIEF DESCRIPTION OF THE INVENTION

In some embodiments of the present invention, a method for reconstructing an image is provided using an imaging apparatus that includes a radiation source, a detector array, and a computer. The method includes performing a helical scan of an object at a selected helical pitch using the radiation source and detector array to obtain image data, and reconstructing an image of the object utilizing the computer programmed to perform a hybrid cone beam image reconstruction having ray-wise 3D weighting, wherein the weighting is dependent upon both helical pitch and z-distance.

In other embodiments of the present invention, an imaging apparatus for reconstructing an image is provided. The apparatus includes a radiation source, a detector array, and a computer. The apparatus is configured to perform a helical scan of an object at a selected helical pitch using the radiation source and detector array to obtain image data, and reconstruct an image of the object utilizing the computer, wherein the computer is programmed to perform a hybrid cone beam image reconstruction having ray-wise 3D weighting, and wherein the weighting is dependent upon both helical pitch and z-distance.

In yet other embodiments of the present invention, a machine readable medium or media having instructions recorded thereon is provided to instruct an imaging apparatus comprising a radiation source, a detector array, and a computer, to perform a helical scan of an object at a selected helical pitch using the radiation source and detector array to obtain image data, and to reconstruct an image of the object utilizing the computer to perform a hybrid cone beam image reconstruction having ray-wise 3D weighting, wherein the weighting is dependent upon both helical pitch and z-distance.

DETAILED DESCRIPTION OF THE INVENTION

Figure 1:
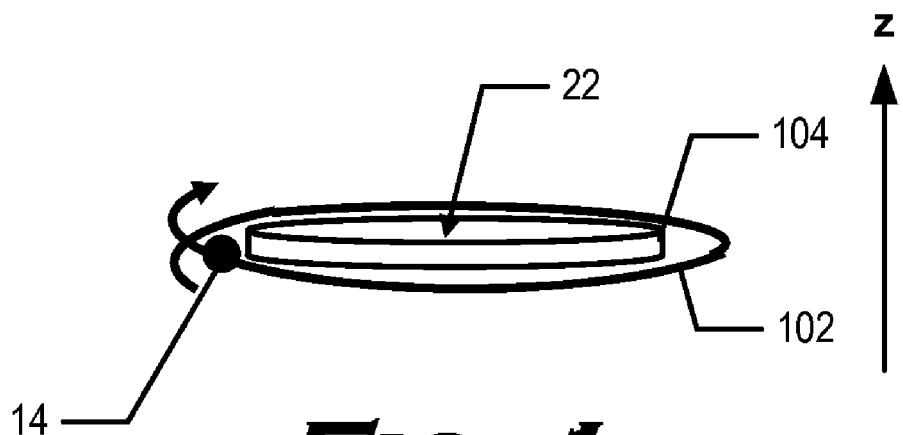
FIG. 1 is a schematic diagram showing a strategy for determining the z-location of image planes in a helical scan with a single helical turn.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like).

Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also, as used herein, the phrase "reconstructing an image" is not intended to exclude embodiments of the present in which data representing an image is generated but a viewable image is not. However, many embodiments generate (or are configured to generate) at least one viewable image.

In some known CT imaging system embodiments, an x-ray source projects a fan-shaped beam that is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to or during a backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to or during the backprojection process.

Figure 2:
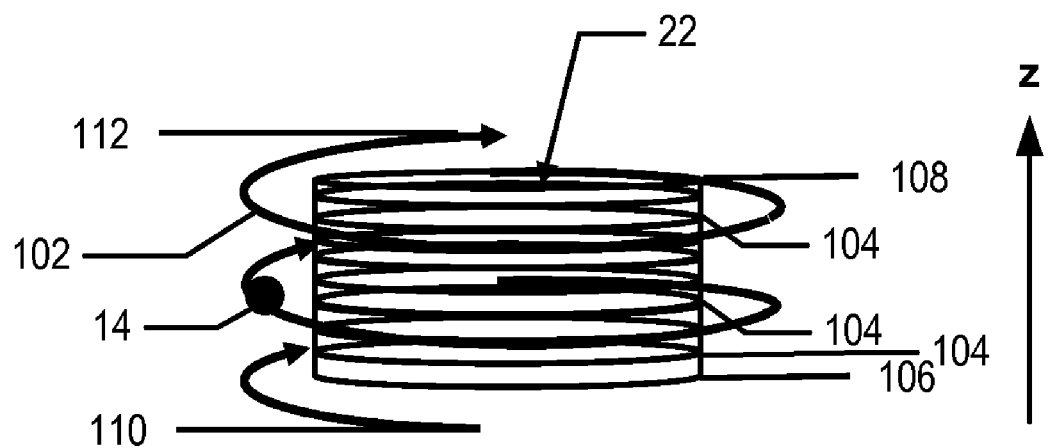
FIG. 2 is a schematic diagram showing a strategy for determining the z-location of image planes in a helical scan with a plurality of helical turns.
Figure 3:
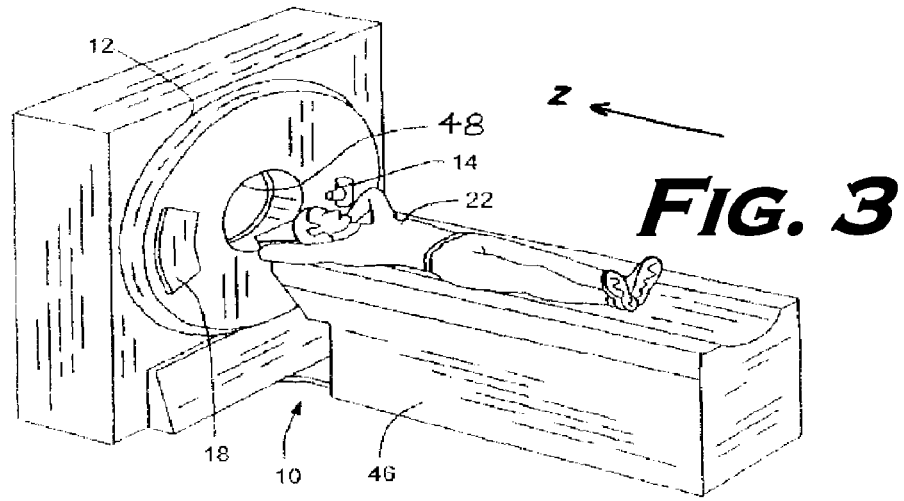
FIG. 3 is a pictorial diagram of an exemplary computed tomographic (CT) imaging system embodiment of the present invention.
Figure 4:
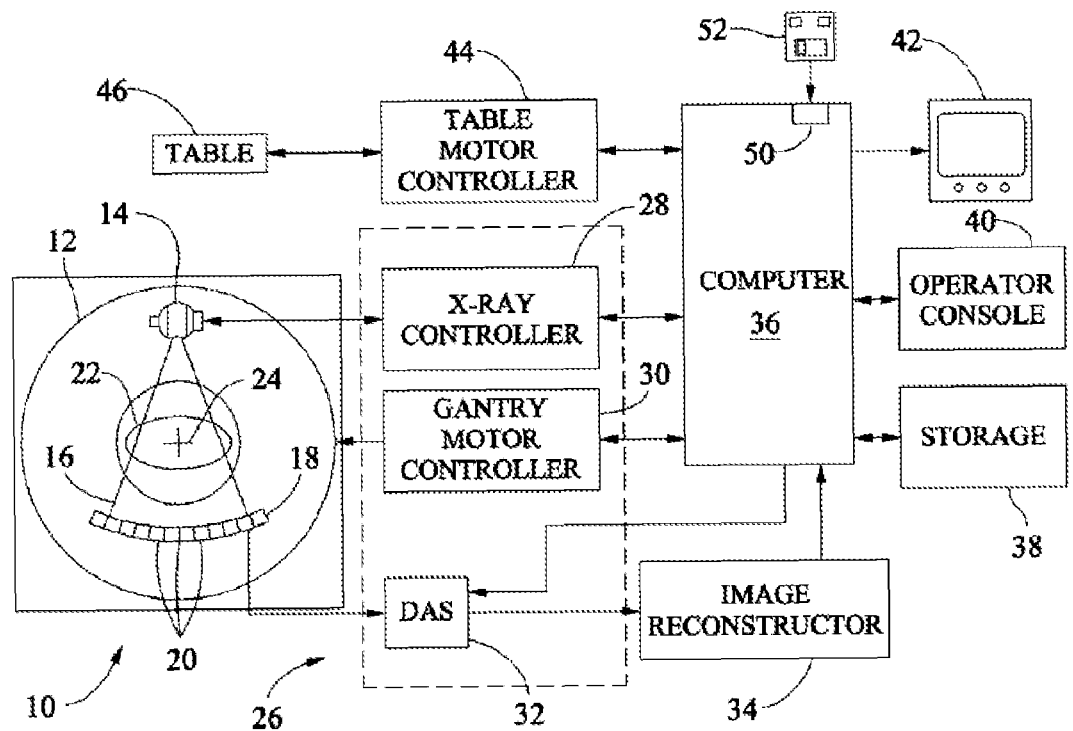
FIG. 4 is a pictorial block diagram of the exemplary CT imaging system shown in FIG. 3.

Referring to FIG. 3 and FIG. 4, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 or other suitable display type allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein apply equally to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Some embodiments of the present invention provide a ray-wise 3D weighting that depends upon both helical pitch and z-distance, where z is an axis perpendicular or essentially perpendicular to the rotation of gantry 12. In the case of imaging systems not having a rotating gantry, z is perpendicular or essentially perpendicular to the plane of an image slice. A technical effect of such weighting is that a conventional indented image zone in a helical scan can be extended substantially as compared to other known weightings. Consequentially, the dose efficiency in volumetric CT in helical scans can be improved significantly, especially in clinical applications in which the helical pitch is relatively low.

Thus, some embodiments of the present invention comprise a hybrid CB-FBP algorithm using ray-wise 3D weighting. The hybrid algorithm reconstructs images beyond the conventional indented image zone by combining helical and axial versions of a ray-wise 3D weighted CB-FBP algorithm. More specifically, the ray-wise 3D weighting in embodiments of the hybrid CB-FBP algorithm are dependent upon both helical pitch and z-distance l. Consequently, the number of tomographic images covering anatomic structures irradiated by x-rays (or other radiation) can be as increased, and indentions in image zones can be reduced.

Figure 5:
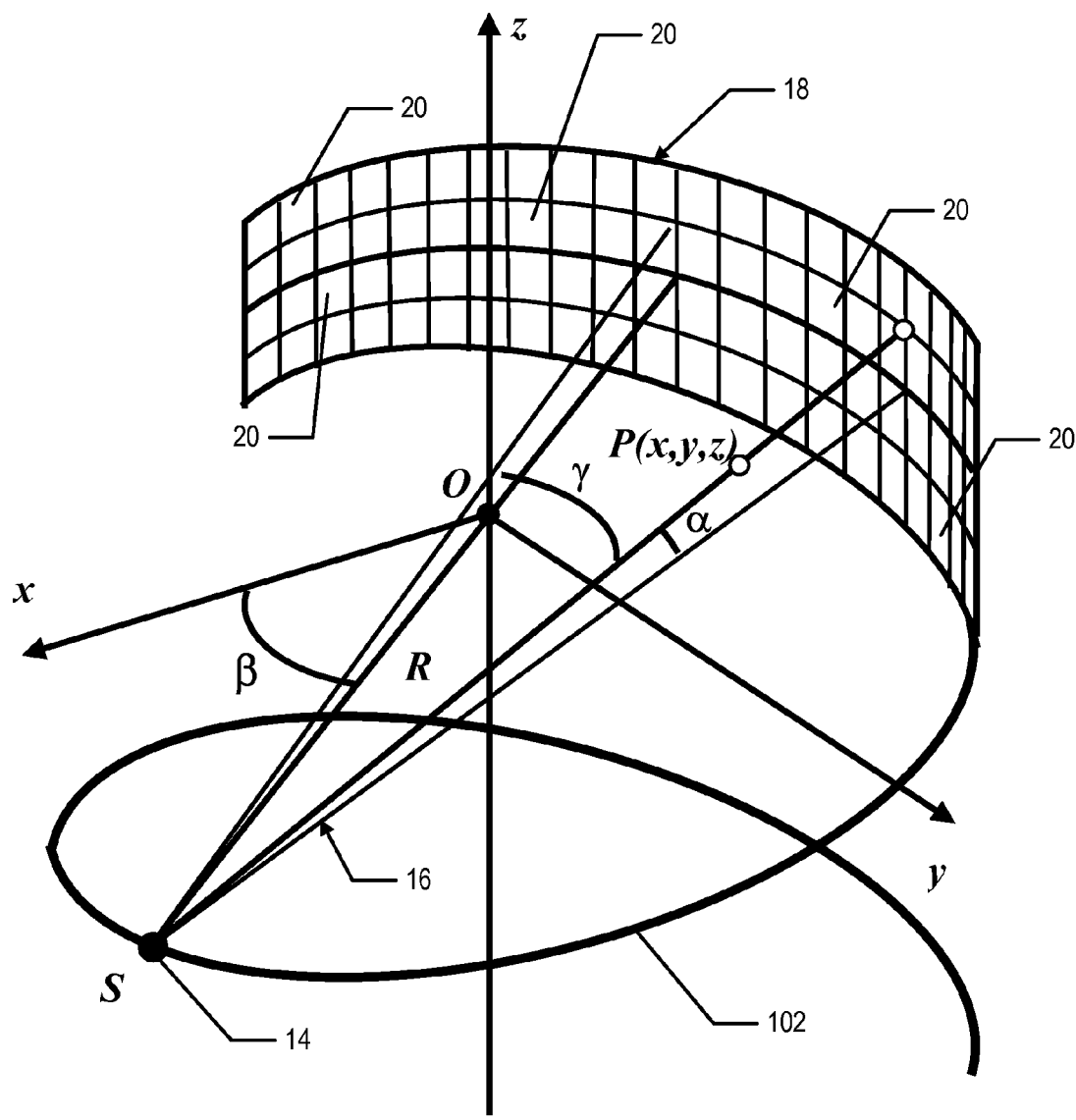
FIG. 5 is a schematic illustration of helical scanning in a native cone beam geometry.
Figure 6:
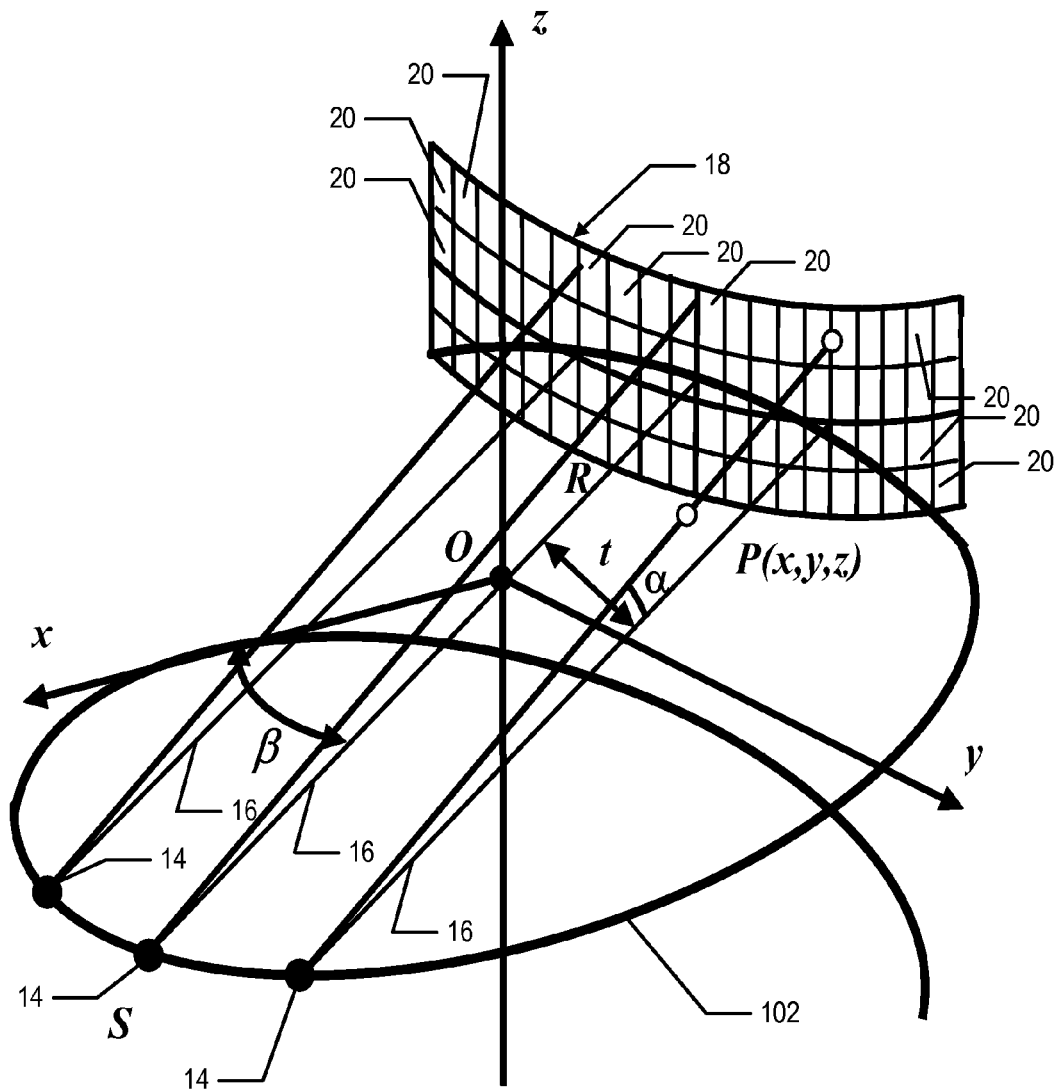
FIG. 6 is a schematic illustration of the same helical scanning as FIG. 5, but in a cone-parallel geometry obtained by row-wise fan-to-parallel rebinning from the native cone beam geometry.
Figure 7:
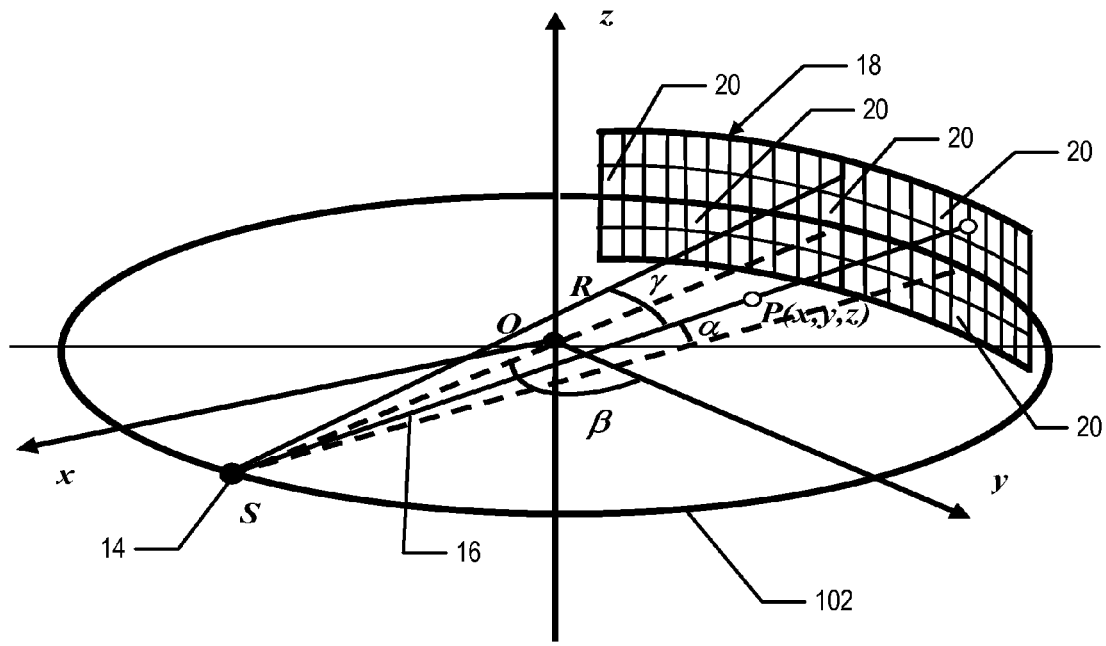
FIG. 7 is a schematic illustration showing axial scanning in the native cone beam geometry.
Figure 8:
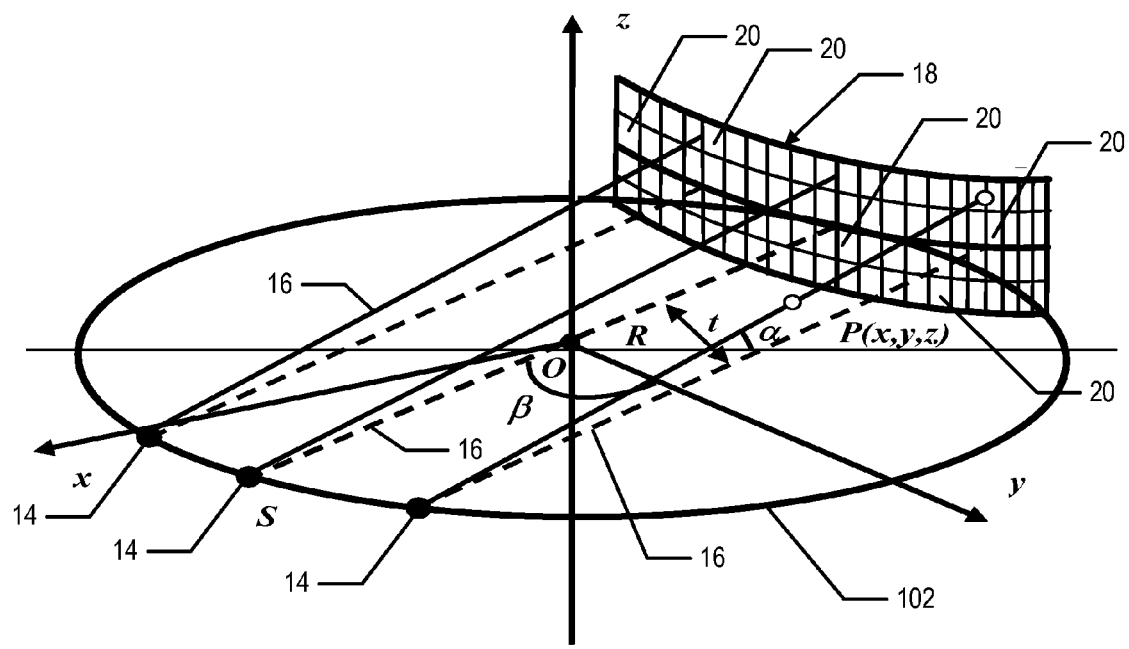
FIG. 8 is a schematic illustration of the same axial scanning as FIG. 7, but in a cone-parallel geometry obtained by row-wise fan-to-parallel rebinning from the native cone beam geometry.

FIG. 5 is a schematic illustration of helical scanning in a native cone beam geometry and FIG. 6 is a schematic illustration of the same helical scanning along a trajectory 102 in a cone-parallel geometry obtained by row-wise fan-to-parallel rebinning from the native cone beam geometry. FIG. 7 and FIG. 8 are, respectively, schematic illustrations showing axial scanning along a trajectory 102 in the native cone beam geometry and a cone-parallel geometry obtained by row-wise fan-to-parallel rebinning from the native cone beam geometry. Note that the curvature of the cylindrical detector 18 in the native CB geometry becomes reversed in the cone-parallel geometry.

Referring to FIG. 5 and FIG. 6, or to FIG. 7 and FIG. 8, a cone beam VCT (CB VCT) imaging system uses, for example, a cylindrical radiation detector array 18 with a plurality of detector elements 20. A radiation beam 16 emanates from a focal spot S of radiation source 14. In many computed tomographic imaging systems 10, radiation detector array 18 is an x-ray detector array, radiation beam 16 is an x-ray beam, and radiation source 14 is an x-ray source, and will be referred to as such herein. However, configurations of the present invention are not limited to the use of x-ray radiation. X-ray beam 16 passes through a point P(x, y, z) and has a view angle $\beta$, a fan angle $\gamma$, and a cone angle $\alpha$.

In the native cone beam geometries shown in FIG. 5 and FIG. 7, $O_{xyz}$ denotes the coordinate system, S the x-ray source 14 focal spot, and R the radius of the source trajectory. P(x, y, z) is a point within the object 22 to be reconstructed. The radiation 16 emanating from focal spot S of radiation source 14 and passing through the point P(x, y, z) is uniquely determined by its view angle β, fan angle γ, and cone angle α. Analytically, the axial source trajectory 102 can be written as:

$$ST(\beta) = (R \sin \beta, R \cos \beta, 0) \quad \beta \subseteq [\beta_s, \beta_e], \quad (2)$$

and the helical source trajectory 102 can be written as:

$$ST(\beta) = \left(R\sin\beta, R\cos\beta, \frac{H}{2\pi}\beta\right) \quad \beta \subseteq [\beta_s, \beta_e], \quad (3)$$

where $\beta_s$ and $\beta_e$ represent the starting and ending points of the source trajectories, respectively. H is the distance traveled by the x-ray source 14 focal spot S of radiation source 14 per rotation around the z-axis, and R is the radius of the helical source trajectory 102. An axial scan can be considered as a special case of a helical scan with H=0, $\beta_s$=0, and $\beta_e$=2π. The curvature of the cylindrical detector 18 in the native cone beam (CB) geometry becomes reversed in the cone-parallel geometry.

FIG. 6 (or FIG. 8) shows the determination of an image plane if a helical scan spans just one helical turn. Conventionally, given the projection data acquired within a view angle of 360° (one helical turn), only a single image is reconstructed, and the image plane intercepts the helical trajectory 102 at the midpoint of the helical turn. Thus, the location of a single image must be indented one half a helical turn from the starting and ending points corresponding to view angles $\beta_s$=0 and $\beta_e$=2π, respectively. If the view angle range of projection data in the helical scan is larger than 360°, more than one image is reconstructed. Each image is reconstructed from the projection data acquired along one helical turn (360° in view angle range), and the image plane is always located at the midpoint of the corresponding helical turn. Consequently, the first reconstructed image must still be indented one half helical turn from the starting point corresponding to $\beta_s$, as must the last image from the ending point corresponding to $\beta_e$. Thus, the image zone is always smaller than the scan zone and the difference is equal to the distance proceeded by the x-ray focal spot per helical turn (360° in view angle range). The determination of image planes in this manner is suboptimal from the standpoint of radiation dose efficiency. However, this method for determining image planes satisfies the data sufficiency condition quite well and all images are of the same reconstruction accuracy. However, because an image plane is always located at the midpoint of the corresponding helical turn (360° in view angle range), the projection of the image plane on the detector is symmetric in relationship to the center of the detector along the z-dimension (i.e., detector z-center). Longitudinal truncation in which the projection falls outside of the longitudinal boundary of the detector occurs when the view angle is relatively large, and this truncation may result in severe artifacts if an inappropriate weighting function is used.

A hybrid cone beam image reconstruction using an appropriate ray-wise 3D weighting can be expressed as:

$$\tilde{f}(x, y, z) = \quad (4)$$

$$\frac{\pi}{(\beta_{max} - \beta_{min})} \int_{\beta_{min}}^{\beta_{max}} \frac{R}{\sqrt{R^2 + Z^2}} w_{3d}(\alpha, \beta, t; h, l) \tilde{s}(\alpha, \beta, t) d\beta,$$

$$\tilde{s}(\alpha, \beta, t) = s(\alpha, \beta, t) \otimes q(t) \quad (5)$$

where $s(\alpha, \beta, t)$ is the virtual projection in the cone-parallel geometry, and α, β, t are the cone angle, view angle and orthogonal iso-distance corresponding to the ray 16 passing through the point to be reconstructed. q(t) represents the one dimensional (1D) ramp filtering kernel, and ⊗ the 1D convolution operator. h is the normalized helical pitch, and the ray-wise 3D weighting function is defined as $$w_{3d}(\alpha, \beta, t; h, l) = \frac{w_{2d}(\beta, t)g(\alpha_c; h, l)}{w_{2d}(\beta, t)g(\alpha_c; h, l) + w_{2d}(\beta_c, t_c)g(\alpha; h, l)} \quad (6)$$

where $\alpha_c, \beta_c, t_c$ are the cone angle, view angle and orthogonal iso-distance corresponding to the conjugate ray passing through the point to be reconstructed. $w_{2d}(\beta, t)$ is a 2D view weighting function that has been extensively utilized in fan beam and cone beam image reconstructions. An example of a particular embodiment of ray-wise 3D weighting function is written:

$$w_{3d}(\alpha, \beta, t; h, l) = \frac{w_{2d}(\beta, t)\tan^{k(h,l)}(\alpha_c)}{w_{2d}(\beta, t)\tan^{k(h,l)}(\alpha_c) + w_{2d}(\beta_c, t_c)\tan^{k(h,l)}(\alpha)}, \quad (7)$$

where k is a parameter that is dependent upon the normalized helical pitch h and can be empirically determined via experimental trial.

The ray-wise 3D weighting function is provided to track the projection of the extended image slice appropriately, so that the complicated longitudinal truncation can be avoided as much as possible. For helical scans, the dependence of the 3D weighting function on helical pitch h and z-distance l of the image slice to be reconstructed is realized by the exponent k(h, l), which can be experimentally determined. A ray-wise 3D weighting function is thus selected that satisfies a suitable normalization condition, such as that written:

$$w_{3d}(\alpha,\beta,t;h,l) + w_{3d}(\alpha_c,\beta_c,t_c;h,l) = 1.0 \quad (8)$$

In cone-parallel geometry, the ray-wise 3D weighting function $w_{3d}(\alpha,\beta,t;h,l)$ is dependent upon the view angle β, orthogonal iso-distance t and cone angle α. It is the dependence on cone angle α that deals with deteriorated longitudinal truncation effectively. Also note that the further the image plane is away from the midpoint, the more severe the asymmetry of the projection of the image plane. Hence, in addition to its dependence upon helical pitch h, parameter k should be dependent upon a distance l between the deviated image plane and the midpoint image plane. Parameter k is used mainly to deal with data inconsistency and longitudinal truncation. Parameter k should become larger with increasing distance l.

Figure 9:
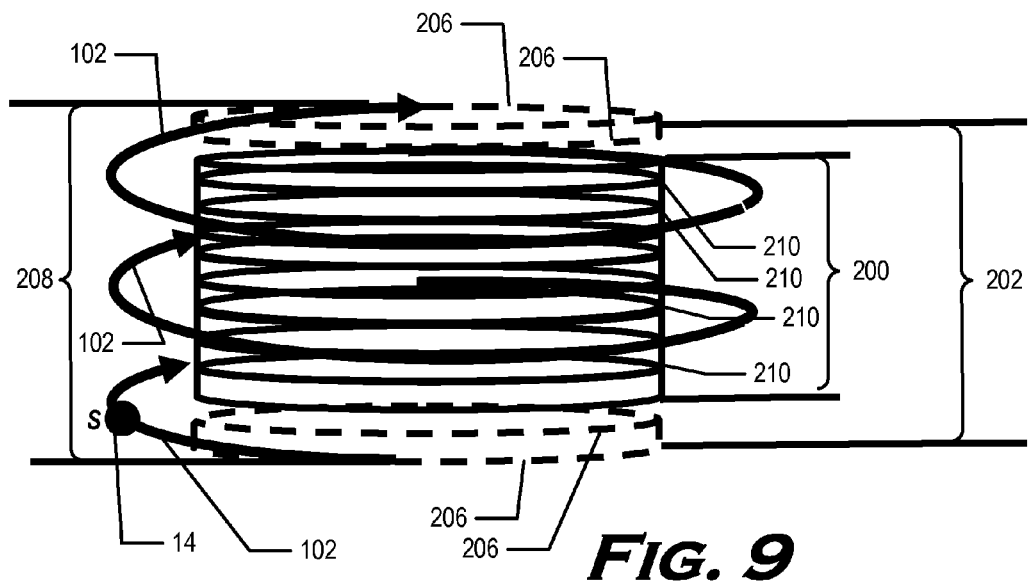
FIG. 9 is a schematic diagram showing how to extend the image zone of a helical scan into an extended image zone by reconstructing additional image slices (shown with dotted lines) at the starting and finishing ends of a scan zone.
Figure 10:
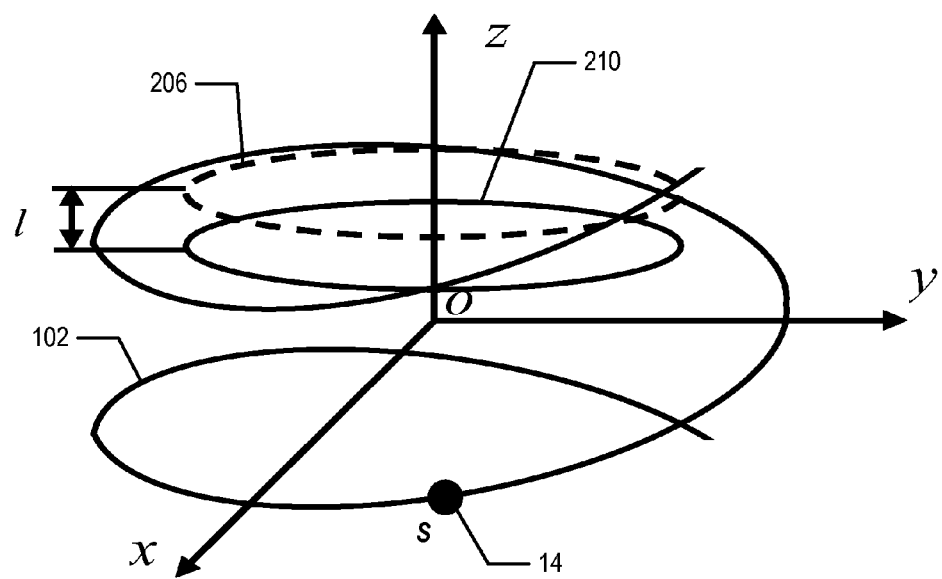
FIG. 10 is an example of an extended image slice 206 at z-distance l away from either a first or a last mid-way image slice.

FIG. 9 is a schematic diagram showing the extension of an image zone 200 of a helical scan 204 into an extended image zone 202 by reconstructing additional image slices 206 (shown with dotted lines) at the starting and finishing ends of a scan zone 208. Midrange slices 210 are also shown (with solid lines). By using a ray-wise 3D weighting function $w_{3d}(\alpha,\beta,t;h,l)$ that is dependent upon the view angle β, orthogonal iso-distance t and cone angle α, suitable images without excessive artifacts can be obtained up to and including slices 206 at or near the starting and finishing ends of scan zone 208. In previously known image reconstruction methods, excessive artifacts existed at slices 206, and in some cases, even in midrange slices 210. An example of an extended image slice 206 at z-distance l away from either a first or a last mid-way image slice is shown in FIG. 10.

Figure 11:
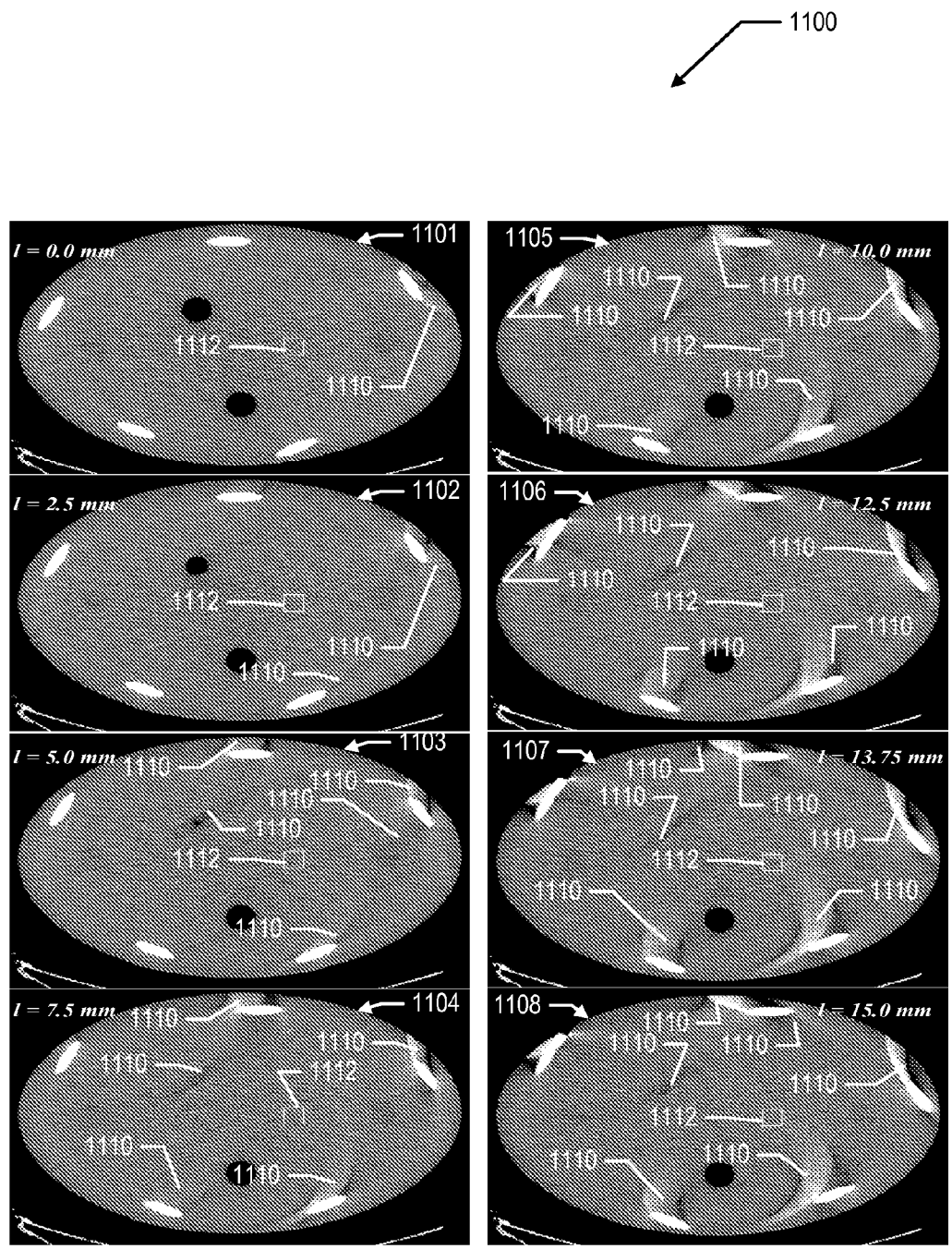
FIG. 11 is a set of transaxial images of a helical body phantom reconstructed by the hybrid method described above using 2D view weighting at various z-distances l (Pitch: 63/64:1, detector z-dimension 64×0.625 mm, display w/l=300/−25 HU).

FIG. 11 is a set 1100 of transaxial images 1101, 1102, 1103, 1104, 1105, 1106, 1107, and 1108 of a helical body phantom reconstructed by the hybrid method described above using 2D view weighting at various z-distances l (Pitch:

63/64:1, detector z-dimension 64×0.625 mm, display w/l=300/−25 HU). A square region 1112 in each of the images of the body phantom represents a location where noise has been measured. With this commonly used helical pitch very close to 1:1, the 2D view weighting results in all images 1101-1108 having substantial and objectionable artifacts 1110, even in image slices at midrange.

Figure 12:
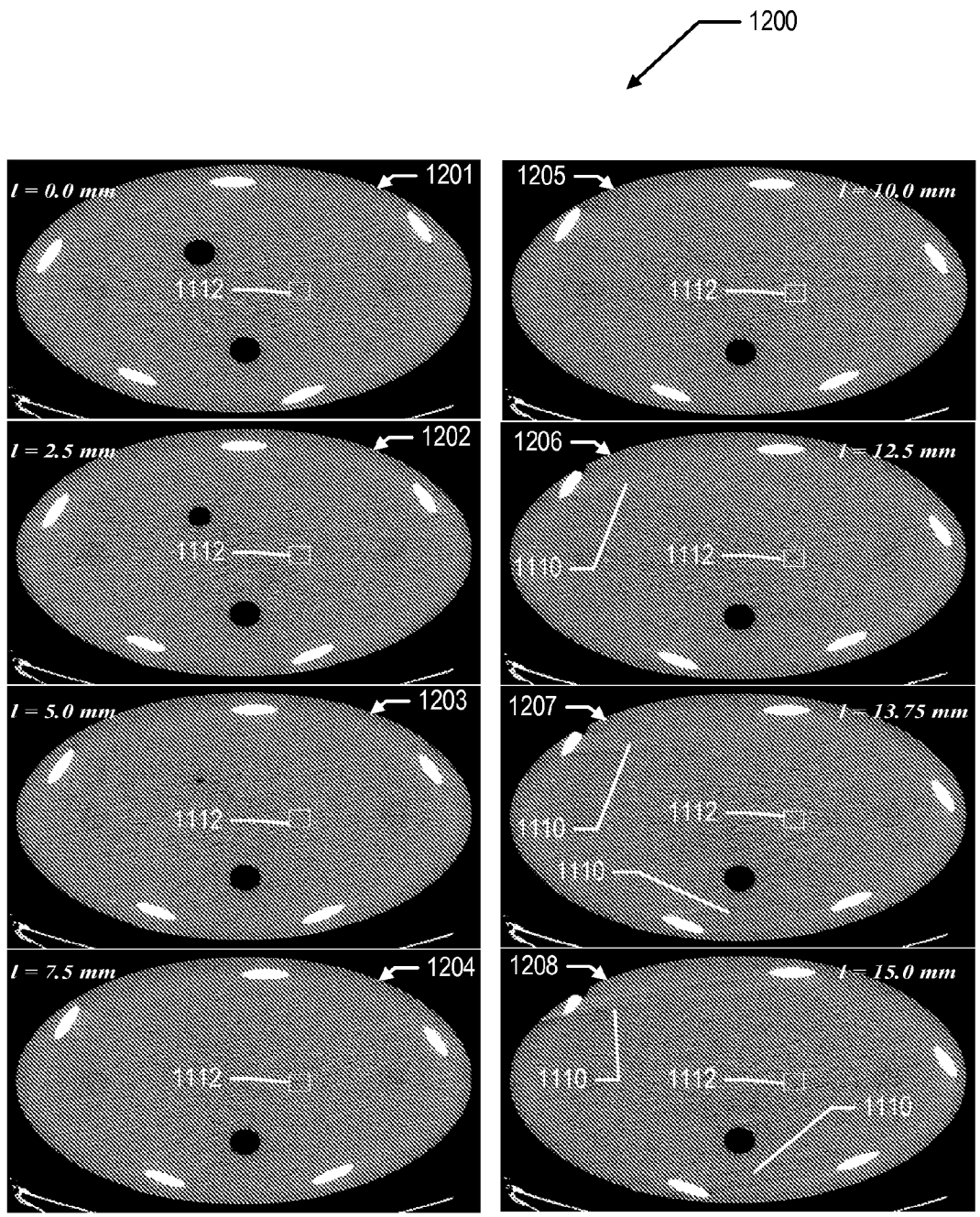
FIG. 12 is a set of transaxial images of the helical body phantom reconstructed by the hybrid algorithm using ray-wise 3D weighting at various z-distances l (Pitch: 63/64:1, detector z-dimension 64×0.625 mm, display w/l=300/−25 HU).

FIG. 12 is a set 1200 of transaxial images 1201, 1202, 1203, 1204, 1205, 1206, 1207, and 1208 of the helical body phantom reconstructed by the hybrid algorithm using ray-wise 3D weighting at various z-distances l (Pitch: 63/64:1, detector z-dimension 64×0.625 mm, display w/l=300/−25 HU). A square region 1112 in each of the images of the body phantom represents a location where noise has been measured. Using hybrid cone beam image reconstruction with ray-wise 3D weighting has improved the image quality of all image slices 1201-1208 substantially, as can seen by the lack of substantial artifacts 1110. Artifacts 1110 that do appear in images 1206, 1207, and 1208 are neither substantial nor objectionable compared to images 1101-1108. For example, the image quality of the extended image slice 1206 at z-distance l=12.5 mm is still satisfactory.

Two helical turns can be taken as a reference to evaluate the improvement in x-ray dose efficiency. Without image zone extension, the z-dimension of the image zone is 63×0.625=39.375 mm. By employing the hybrid cone beam image reconstruction using ray-wise 3D weighting, the z-dimension of the extended image zone is 39.375+2×12.5=64.375 mm. Consequently, the improvement in x-ray dose efficiency for the image set 1200 over that of image set 1100 is $$\frac{64.375 - 39.375}{39.375} \times 100\% = \frac{25}{39.375} \times 100\% \approx 63.5\% \quad (9)$$

and this is indeed a significant gain in x-ray dose efficiency of helical scan in volumetric CT.

Figure 13:
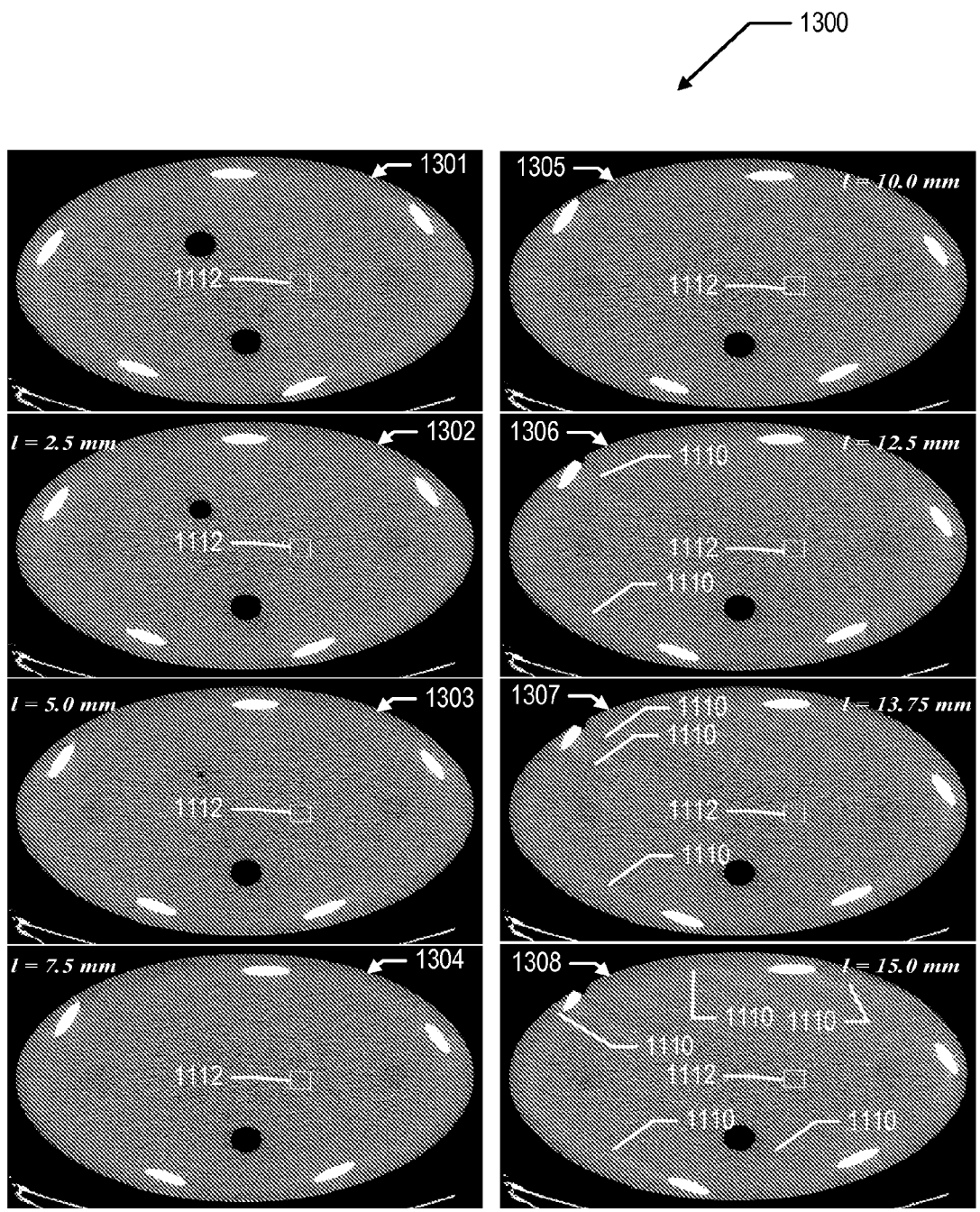
FIG. 13 is a set of transaxial images of the helical body phantom reconstructed by the hybrid algorithm using ray-wise 3D weighting at various z-distances l (Pitch: 88/64:1, detector z-dimension 64×0.625 mm, display w/l=300/−25 HU).

FIG. 13 is a set 1300 of transaxial images 1301, 1302, 1303, 1304, 1305, 1306, 1307, and 1308 of the helical body phantom reconstructed by the hybrid algorithm using ray-wise 3D weighting at various z-distances l (Pitch: 88/64:1, detector z-dimension 64×0.625 mm, display w/l 300/−25 HU). A square region 1112 in each of the images of the body phantom represents a location where noise has been measured. This test scan was performed to evaluate the robustness of the hybrid cone beam image reconstruction using ray-wise 3D weighting. Images at z-distances l equal to those in FIG. 11 and FIG. 12 are presented in FIG. 13. Helical pitch 88/64:1 is significantly larger than helical pitch 63/64:1, but the hybrid cone beam image reconstruction can still provide satisfactory image quality at image 1306, i.e., the image at z-distance 12.5 mm. Only relatively mild artifacts 1110 can be seen in images 1306, 1307, and 1308.

If two helical turns are again used as a reference of evaluating x-ray dose efficiency, such an extension in image zone corresponds to an improvement in x-ray dose efficiency of $$\frac{12.5 \times 2}{88 \times 0.625} \times 100\% = \frac{25}{55} \times 100\% \approx 45.5\%, \quad (10)$$

which is still a significant gain from the perspective of clinical applications.

In addition, the hybrid cone beam image reconstruction embodiments disclosed herein can be combined with the technique of using pre-patient collimator in the starting and ending points of a helical scan, so that the radiation dose rendered to the over-beamed zone can be reduced further. Moreover, in another embodiment, a variable table speed is used at the starting and ending point of a helical scan. Thus, the helical scan can start at table speed 0.0 mm/s and then accelerate to reach a specified constant helical pitch, and end by decelerating from the specified constant pitch to reach a table speed 0.0 mm/s. This scan mode can be considered a combination of constant and variable helical pitch scans. By adjusting the acceleration and deceleration, as well as the parameters k(h, l), appropriately, the conventional image zone may be extended to be equal to the scan zone, i.e., no over-beamed zone at all.

Figure 14:
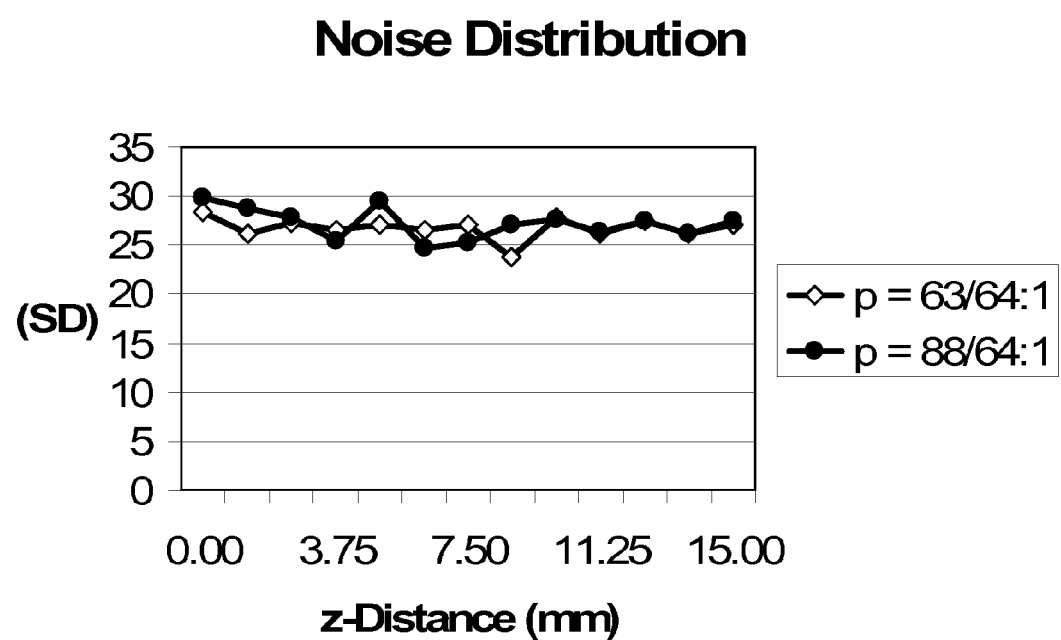
FIG. 14 is a plot of the noise distribution of midrange image slice and extended image slices as a function over z-distance l (slice thickness: 0.625 mm).

FIG. 14 is a plot of the noise distribution of midrange image slice and extended image slices as a function over z-distance l (slice thickness: 0.625 mm) for the image sets 1200 and 1300 having the pitches indicated in the legend. Hybrid cone beam image reconstruction using ray-wise 3D weighting not only can extend the image zone of helical scan in volumetric CT, but can also maintain a relatively uniform noise distribution over z-distance as demonstrated by FIG. 14. Note that noise characteristics of extended image slices are comparable with those of mid-way slices, an important advantage in clinical applications.

To summarize, some embodiments of the present invention provide a method for reconstructing an image using an imaging apparatus 10 comprising a radiation source 14, a detector array 18, and a computer. The "computer" in this sense is construed to encompass any peripheral and/or external devices that aid in computing and/or displaying results. For example, the computer of this embodiment may include not only computer 36 of FIG. 4, but also image reconstructor 34, storage 38, operator console 40, media reader 50, and display 42. The method includes performing a helical scan of an object at a selected helical pitch using the radiation source and detector array to obtain image data, and reconstructing an image of the object utilizing the computer programmed to perform a hybrid cone beam image reconstruction having ray-wise 3D weighting, wherein the weighting is dependent upon both helical pitch and z-distance.

In some embodiments, the imaging apparatus is a computed tomography (CT) imaging system 10, the radiation source is an x-ray source 14, and the detector array 18 is a multi-slice detector array. Also, in some embodiments, reconstructing an image of object 22 utilizing a computer further comprises applying a hybrid cone beam image reconstruction using a ray-wise 3D weighting, wherein the reconstruction is written:

$$\tilde{f}(x, y, z) = \frac{\pi}{(\beta_{max} - \beta_{min})} \int_{\beta_{min}}^{\beta_{max}} \frac{R}{\sqrt{R^2 + Z^2}} w_{3d}(\alpha, \beta, t; h, l) \tilde{s}(\alpha, \beta, t) d\beta$$

$$\tilde{s}(\alpha, \beta, t) = s(\alpha, \beta, t) \otimes q(t),$$

where $s(\alpha, \beta, t)$ is the virtual projection in the cone-parallel geometry, and $\alpha$, $\beta$, t are the cone angle, view angle and orthogonal iso-distance corresponding to the ray passing through a point to be reconstructed, q(t) represents a one dimensional (1D) ramp filtering kernel, ⊗represents the 1D convolution operator, h is the normalized helical pitch, and the ray-wise 3D weighting function is written:

$$w_{3d}(\alpha, \beta, t; h, l) = \frac{w_{2d}(\beta, t)g(\alpha_c; h, l)}{w_{2d}(\beta, t)g(\alpha_c; h, l) + w_{2d}(\beta_c, t_c)g(\alpha; h, l)}$$

where $\alpha_c$, $\beta_c$, and $t_c$ are, respectively, a cone angle, view angle and orthogonal iso-distance corresponding to a conjugate ray passing through the point to be reconstructed, and $w_{2d}(\beta, t)$ is a 2D view weighting function.

In some of these embodiments, the ray-wise helical weighting function is written:

$$w_{3d}(\alpha, \beta, t; h, l) = \frac{w_{2d}(\beta, t)\tan^{k(h,l)}(\alpha_c)}{w_{2d}(\beta, t)\tan^{k(h,l)}(\alpha_c) + w_{2d}(\beta_c, t_c)\tan^{k(h,l)}(\alpha)},$$

where k is a parameter that is dependent upon the normalized helical pitch h. In some embodiments, parameter k is determined empirically via experimental trial. An extended image zone is provided in some embodiments of the present invention, and in some embodiments, the selected helical pitch is between about 0.45:1 and about 1.5:1.

In some other embodiments, an imaging apparatus for reconstructing an image is provided. The apparatus includes a radiation source, a detector array, and a computer. In still other embodiments, a machine readable medium or media is/are provided, wherein instructions are recorded to instruct an imaging apparatus to perform an embodiment of the methods described herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for reconstructing an image using an imaging apparatus comprising a radiation source, a detector array, and a computer, said method comprising:
    performing a helical scan of an object at a selected helical pitch using the radiation source and detector array to obtain image data; and
    reconstructing an image of the object utilizing the computer programmed to perform a hybrid cone beam image reconstruction having ray-wise 3D weighting, wherein the weighting is dependent upon both helical pitch and z-distance.

2. The method of claim 1 wherein the imaging apparatus is a computed tomography (CT) imaging system, the radiation source is an x-ray source, and the detector array is a multi-slice detector array.

3. The method of claim 1 wherein said reconstructing an image of the object utilizing a computer further comprises applying a hybrid cone beam image reconstruction using a ray-wise 3D weighting, wherein the reconstruction is written:

$$\tilde{f}(x, y, z) = \frac{\pi}{(\beta_{max} - \beta_{min})} \int_{\beta_{min}}^{\beta_{max}} \frac{R}{\sqrt{R^2 + Z^2}} w_{3d}(\alpha, \beta, t; h, l) \tilde{s}(\alpha, \beta, t) d\beta$$

$$\tilde{s}(\alpha, \beta, t) = s(\alpha, \beta, t) \otimes q(t)$$

where $s(\alpha, \beta, t)$ is the virtual projection in the cone-parallel geometry, and $\alpha$, $\beta$, t are the cone angle, view angle and orthogonal iso-distance corresponding to the ray passing through a point to be reconstructed, q(t) represents a one dimensional (1D) ramp filtering kernel, ⊗ represents the 1D convolution operator, h is the normalized helical pitch, and the ray-wise 3D weighting function is written:

$$w_{3d}(\alpha, \beta, t; h, l) = \frac{w_{2d}(\beta, t)g(\alpha_c; h, l)}{w_{2d}(\beta, t)g(\alpha_c; h, l) + w_{2d}(\beta_c, t_c)g(\alpha; h, l)}$$

where $\alpha_c$, $\beta_c$, and $t_c$ are, respectively, a cone angle, view angle and orthogonal iso-distance corresponding to a conjugate ray passing through the point to be reconstructed, and $w_{2d}(\beta, t)$ is a 2D view weighting function.

4. The method of claim 3 further wherein the ray-wise helical weighting function is written:

$$w_{3d}(\alpha, \beta, t; h, l) = \frac{w_{2d}(\beta, t)\tan^{k(h,l)}(\alpha_c)}{w_{2d}(\beta, t)\tan^{k(h,l)}(\alpha_c) + w_{2d}(\beta_c, t_c)\tan^{k(h,l)}(\alpha)},$$

where k is a parameter that is dependent upon the normalized helical pitch h.

5. The method of claim 4 further comprising determining parameter k empirically via experimental trial.

6. The method of claim 1 used to provide an extended image zone.

7. The method of claim 1 wherein the selected helical pitch is between about 0.45:1 and about 1.5:1.

8. An imaging apparatus for reconstructing an image, said apparatus comprising a radiation source, a detector array, and a computer, and said apparatus configured to:
    perform a helical scan of an object at a selected helical pitch using the radiation source and detector array to obtain image data; and
    reconstruct an image of the object utilizing the computer, said computer programmed to perform a hybrid cone beam image reconstruction having ray-wise 3D weighting, wherein the weighting is dependent upon both helical pitch and z-distance.

9. The apparatus of claim 8 wherein the apparatus is a computed tomography (CT) imaging system, the radiation source is an x-ray source, and the detector array is a multi-slice detector array.

10. The apparatus of claim 8 wherein to reconstruct an image of the object utilizing the computer, the computer is further programmed to apply a hybrid cone beam image reconstruction using a ray-wise 3D weighting, wherein the reconstruction is written:

$$\tilde{f}(x, y, z) = \frac{\pi}{(\beta_{max} - \beta_{min})} \int_{\beta_{min}}^{\beta_{max}} \frac{R}{\sqrt{R^2 + Z^2}} w_{3d}(\alpha, \beta, t; h, l) \tilde{s}(\alpha, \beta, t) d\beta$$

$$\tilde{s}(\alpha, \beta, t) = s(\alpha, \beta, t) \otimes q(t)$$

where $s(\alpha, \beta, t)$ is the virtual projection in the cone-parallel geometry, and $\alpha, \beta, t$ are the cone angle, view angle and orthogonal iso-distance corresponding to the ray passing through a point to be reconstructed, $q(t)$ represents a one dimensional (1D) ramp filtering kernel, $\otimes$ represents the 1D convolution operator, h is the normalized helical pitch, and the ray-wise 3D weighting function is written:

$$w_{3d}(\alpha, \beta, t; h, l) = \frac{w_{2d}(\beta, t)g(\alpha_c; h, l)}{w_{2d}(\beta, t)g(\alpha_c; h, l) + w_{2d}(\beta_c, t_c)g(\alpha; h, l)}$$

where $\alpha_c, \beta_c,$ and $t_c$ are, respectively, a cone angle, view angle and orthogonal iso-distance corresponding to a conjugate ray passing through the point to be reconstructed, and $w_{2d}(\beta, t)$ is a 2D view weighting function.

11. The apparatus of claim 10 further wherein the ray-wise helical weighting function is written:

$$w_{3d}(\alpha, \beta, t; h, l) = \frac{w_{2d}(\beta, t)\tan^{k(h,l)}(\alpha_c)}{w_{2d}(\beta, t)\tan^{k(h,l)}(\alpha_c) + w_{2d}(\beta_c, t_c)\tan^{k(h,l)}(\alpha)},$$

where k is a parameter that is dependent upon the normalized helical pitch h.

12. The apparatus of claim 11 wherein parameter k is determined empirically via experimental trial.

13. The apparatus of claim 8 further configured to provide an extended image zone.

14. The apparatus of claim 8 wherein the selected helical pitch is between about 0.45:1 and about 1.5:1.

15. A non-transitory computer readable medium or media having instructions recorded thereon to instruct an imaging apparatus comprising a radiation source, a detector array, and a computer, to:

perform a helical scan of an object at a selected helical pitch using the radiation source and detector array to obtain image data; and reconstruct an image of the object utilizing the computer to perform a hybrid cone beam image reconstruction having ray-wise 3D weighting, wherein the weighting is dependent upon both helical pitch and z-distance.

16. The medium or media of claim 15 wherein to reconstruct an image of the object utilizing the computer, said medium or media further having instructions recorded thereon to instruct the computer to apply a hybrid cone beam image reconstruction using a ray-wise 3D weighting, wherein the reconstruction is written:

$$\tilde{f}(x, y, z) = \frac{\pi}{(\beta_{max} - \beta_{min})} \int_{\beta_{min}}^{\beta_{max}} \frac{R}{\sqrt{R^2 + Z^2}} w_{3d}(\alpha, \beta, t; h, l) \tilde{s}(\alpha, \beta, t) d\beta$$

$$\tilde{s}(\alpha, \beta, t) = s(\alpha, \beta, t) \otimes q(t)$$

where $s(\alpha, \beta, t)$ is the virtual projection in the cone-parallel geometry, and $\alpha, \beta, t$ are the cone angle, view angle and orthogonal iso-distance corresponding to the ray passing through a point to be reconstructed, $q(t)$ represents a one dimensional (1D) ramp filtering kernel, $\otimes$ represents the 1D convolution operator, h is the normalized helical pitch, and the ray-wise 3D weighting function is written:

$$w_{3d}(\alpha, \beta, t; h, l) = \frac{w_{2d}(\beta, t)g(\alpha_c; h, l)}{w_{2d}(\beta, t)g(\alpha_c; h, l) + w_{2d}(\beta_c, t_c)g(\alpha; h, l)}$$

where $\alpha_c, \beta_c,$ and $t_c$ are, respectively, a cone angle, view angle and orthogonal iso-distance corresponding to a conjugate ray passing through the point to be reconstructed, and $w_{2d}(\beta, t)$ is a 2D view weighting function.

17. The medium or media of claim 16 further wherein the ray-wise helical weighting function is written:

$$w_{3d}(\alpha, \beta, t; h, l) = \frac{w_{2d}(\beta, t)\tan^{k(h,l)}(\alpha_c)}{w_{2d}(\beta, t)\tan^{k(h,l)}(\alpha_c) + w_{2d}(\beta_c, t_c)\tan^{k(h,l)}(\alpha)},$$

where k is a parameter that is dependent upon the normalized helical pitch h.

18. The medium or media of claim 17 wherein parameter k is determined empirically via experimental trial.

19. The medium or media of claim 15 further having instructions recorded thereon configured to instruct the computer to provide an extended image zone.

20. The medium or media of claim 15 wherein the selected helical pitch is between about 0.45:1 and about 1.5:1.

* * * * *